(12) United States Patent
     Baynham

(10) Patent No.: US 12,678,290 B2
(45) Date of Patent: Jul. 14, 2026

(54) FACET JOINT FIXATION DEVICE

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 0 days.

(21) Appl. No.: 18/965,551

(22) Filed: Dec. 2, 2024

(65) Prior Publication Data

US 2026/0151237 A1 Jun. 4, 2026

(51) Int. Cl.
     *A61F 2/44* (2006.01)
     *A61B 17/70* (2006.01)
(52) U.S. Cl.
     CPC ........ *A61F 2/4405* (2013.01); *A61B 17/7064* (2013.01)
(58) Field of Classification Search
     CPC ..................... A61F 2/44–447; A61B 17/7064
     See application file for complete search history.

(56) References Cited

U.S. PATENT DOCUMENTS

| | | | | |
|---|---|---|---|---|
| 5,888,222 | A * | 3/1999 | Coates | A61L 31/06 623/17.16 |
| 9,629,727 | B2 | 4/2017 | Baynham | |
| 2007/0050032 | A1* | 3/2007 | Gittings | A61F 2/4425 623/17.13 |
| 2011/0054535 | A1* | 3/2011 | Gephart | A61B 17/7025 606/279 |
| 2014/0277141 | A1* | 9/2014 | Baynham | A61B 17/7064 606/279 |
| 2015/0196400 | A1* | 7/2015 | Dace | A61F 2/4455 623/17.16 |
| 2019/0209215 | A1* | 7/2019 | Baynham | A61B 17/8042 |

\* cited by examiner

*Primary Examiner* — Nicholas J Plionis
(74) *Attorney, Agent, or Firm* — McHale & Slavin, P.A.

(57) ABSTRACT

A facet joint fixation device formed from a flexible wedge shaped implant constructed from a single piece of material. The device is defined by an insert end spaced apart from outer end by first and second side members. Each side support is cut by a series of recesses in diminishing depth defining a living hinge therebetween. The series of recesses are constructed and arranged to adjust flexibility of said implant.

10 Claims, 13 Drawing Sheets

FACET JOINT FIXATION DEVICE

FIELD OF THE INVENTION

The present invention relates generally to surgically-implantable spinal devices and, more specifically, to a facet joint fixation device.

BACKGROUND OF THE INVENTION

It is often desirable to stabilize/immobilize one or more facet joints of the spine of a patient in the treatment of various spinal ailments/defects. Facet arthrodesis is used to fuse a facet joint including a superior facet and an inferior facet in spinal treatment operations. The facet joints, both superior and inferior, are aligned in a way to allow flexion and extension, and to limit rotation. The biomechanical function of each pair of facet joints is to guide and limit movement of the spinal motion segment. In the lumbar spine, for example, the facet joints function to protect the motion segment from anterior shear forces, excessive rotation and flexion. These functions can be disrupted by degeneration, dislocation, fracture, injury, instability from trauma, osteoarthritis, and surgery. In the thoracic spine the facet joints function to restrain the amount of flexion and anterior translation of the corresponding vertebral segment and function to facilitate rotation.

There are numerous implants and associated methods for performing stabilization/immobilization. Conventional implants include bone screws that are threaded through the superior and inferior facets to immobilize the facet joint so as to permit the adjoined bone sections to fuse together.

Applicant's U.S. Pat. No. 9,629,727 issued Apr. 25, 2017 and entitled Pedicle-Based Construct Facet Joint Fixation Device is directed to a flexible, wedge-shaped implant having an insert end spaced apart from an outer end, connected by first and second arcuate side members that form the main support framework of the implant. Each arcuate side member is segmented by a series of equally sized recesses, creating a living hinge structure along the length of the implant.

SUMMARY OF THE INVENTION

Embodiments of the invention are directed, inter alia, to a facet joint fixation device comprising a flexible, wedge-shaped implant that serves as an anchor for a pedicle screw implant, thereby enhancing the stability and fixation within the spinal column. The facet fixation device is preferably constructed from a single, continuous piece of durable material, designed for both flexibility and resilience. This structure includes an insert end spaced apart from an outer end, connected by first and second arcuate side members that form the main support framework of the implant. Each arcuate side member is segmented by a series of recesses, which gradually diminish in size from the insert end to the outer end, creating a living hinge structure along the length of the implant.

These diminishing in size recesses play a crucial role in enabling the device's flexibility, as they define areas where the material can bend while maintaining structural integrity. Due to the consistent thickness retained throughout the living hinge structure, each side member can bend back and forth in a controlled manner, allowing the implant to adapt to varying spinal geometries and movements. This spring hinge-like resilience provides a degree of elasticity that helps the implant absorb and distribute forces, thereby enhancing both the anchoring capability and the overall performance of the pedicle screw implant within the facet joint. By utilizing a living hinge mechanism, the invention offers a robust yet flexible solution for spinal fixation, improving both the ease of insertion and the long-term stability of the device.

Upon insertion, a pedicle screw can be implanted and positioned between the members and the insert end. The flexible members allow a surgeon to gain access from unobstructed angles. The flexible members serve as a guide for ideal placement of a pedicle screw and dramatically increase the resistance to pedicle screw pullout.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
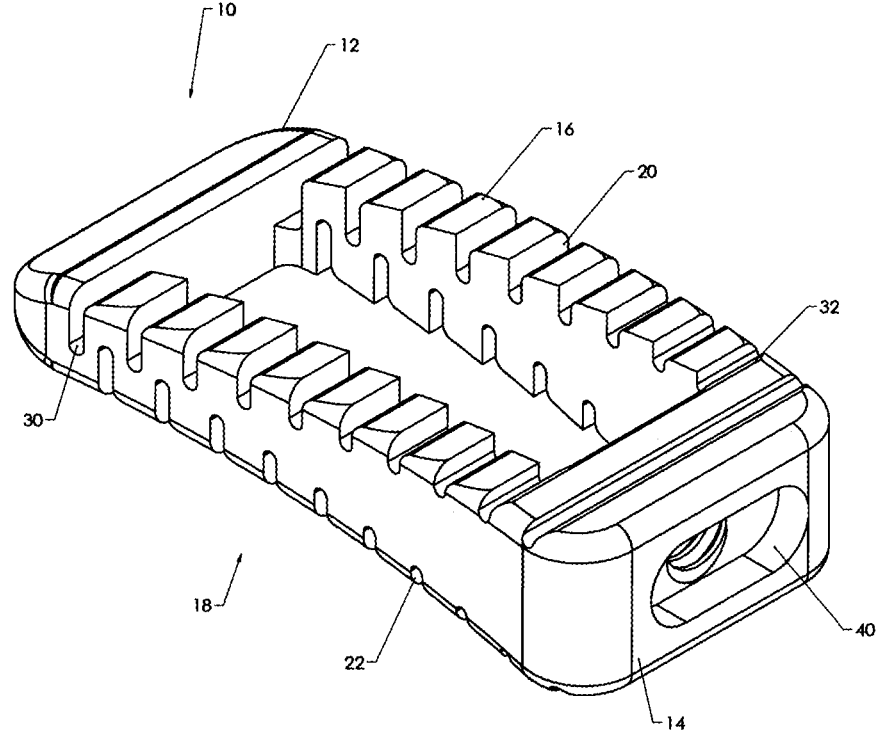
FIG. 1 is a perspective view of the wedge shaped device.
Figure 2:
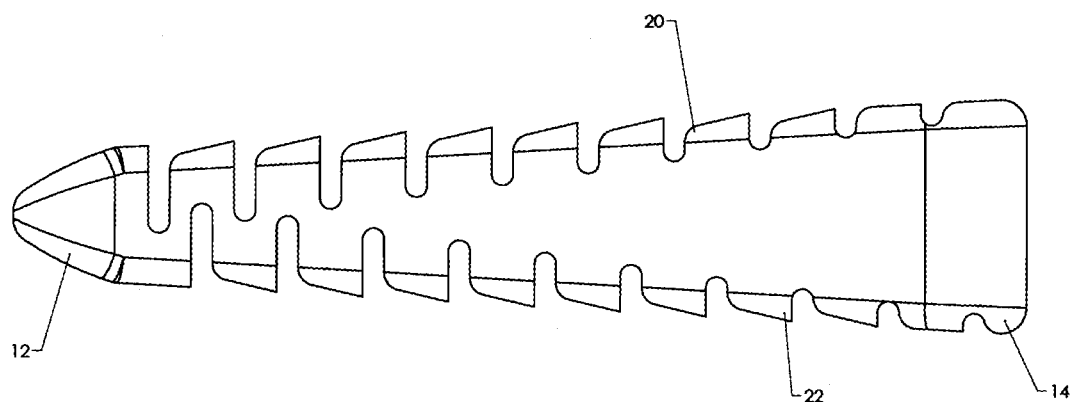
FIG. 2 is a cross-sectional side view thereof.
Figure 3:
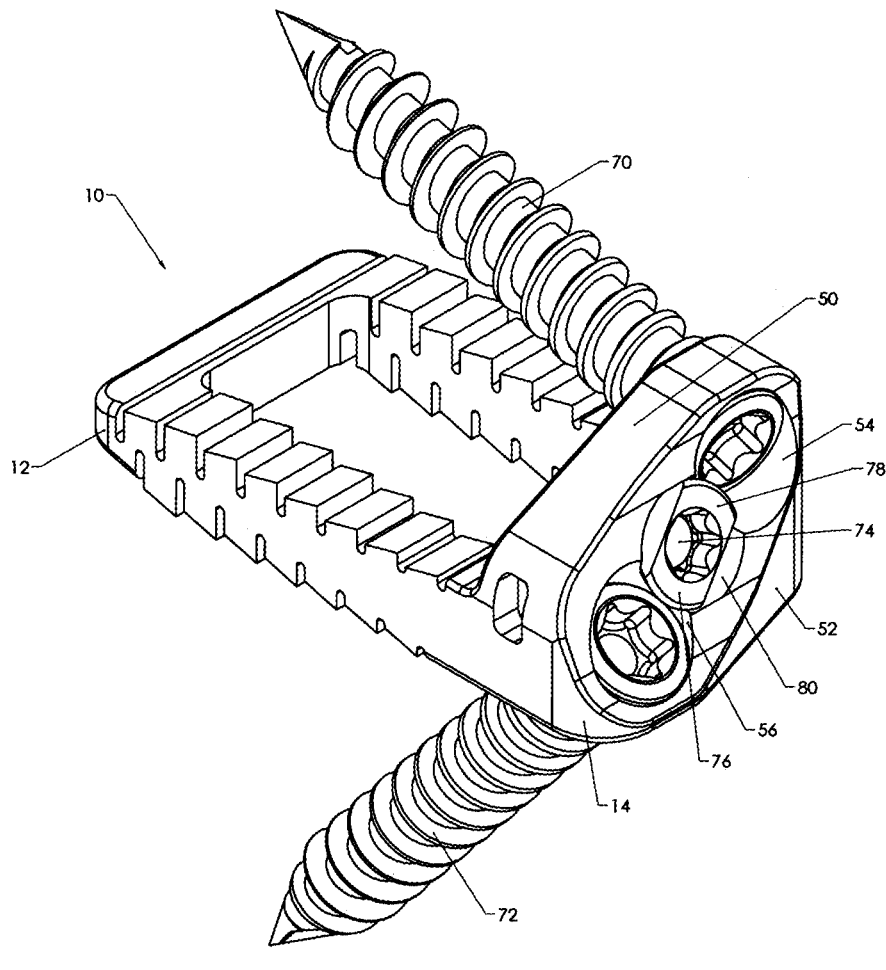
FIG. 3 is a perspective view of another embodiment of the wedge shaped device.
Figure 4:
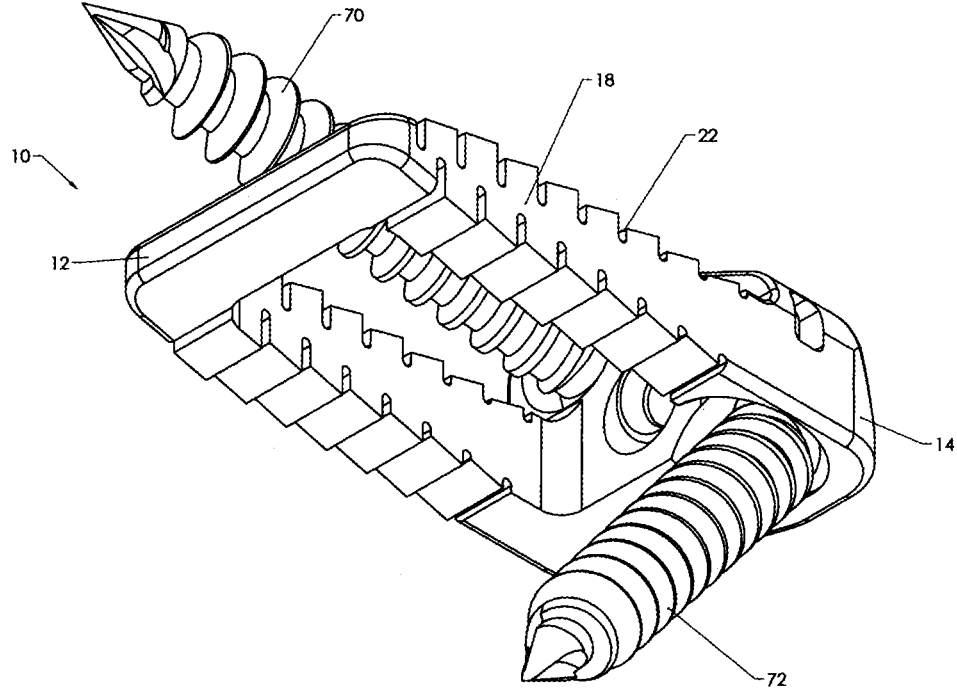
FIG. 4 is a bottom perspective view thereof.
Figure 5:
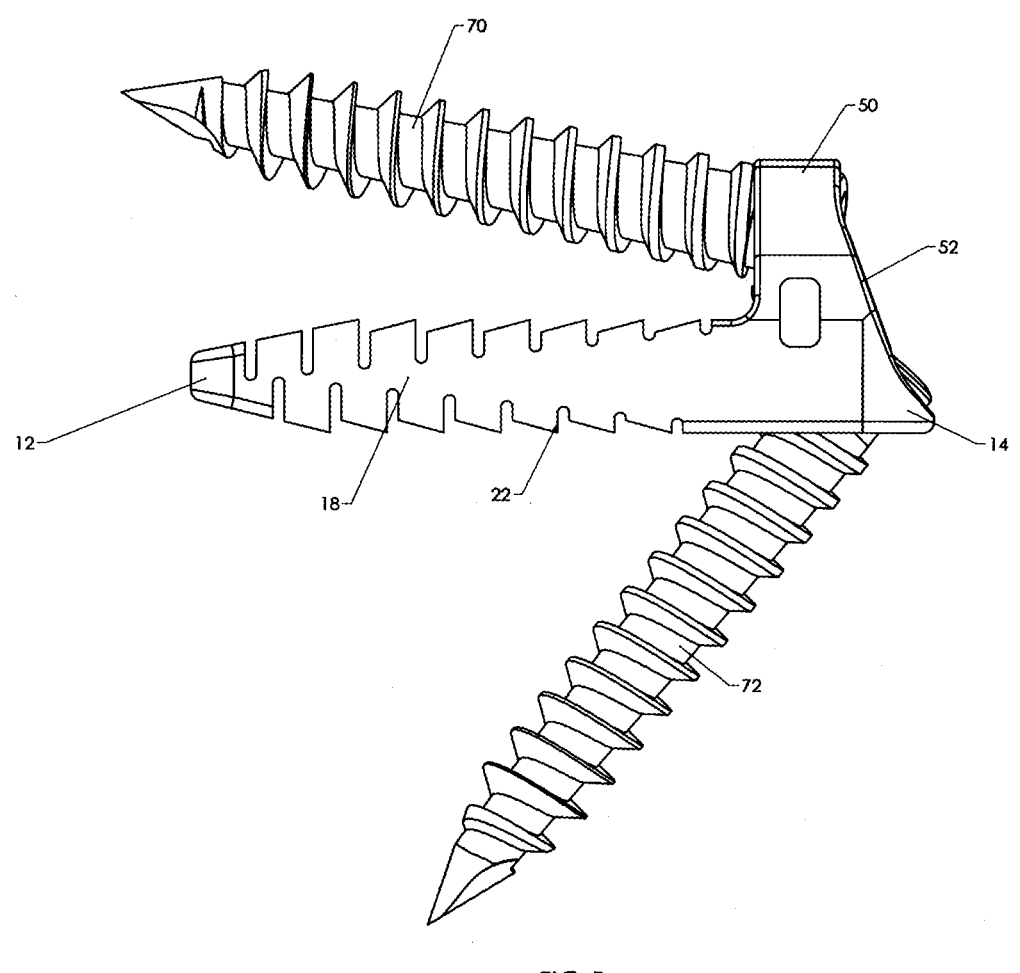
FIG. 5 is a side view thereof.
Figure 6:
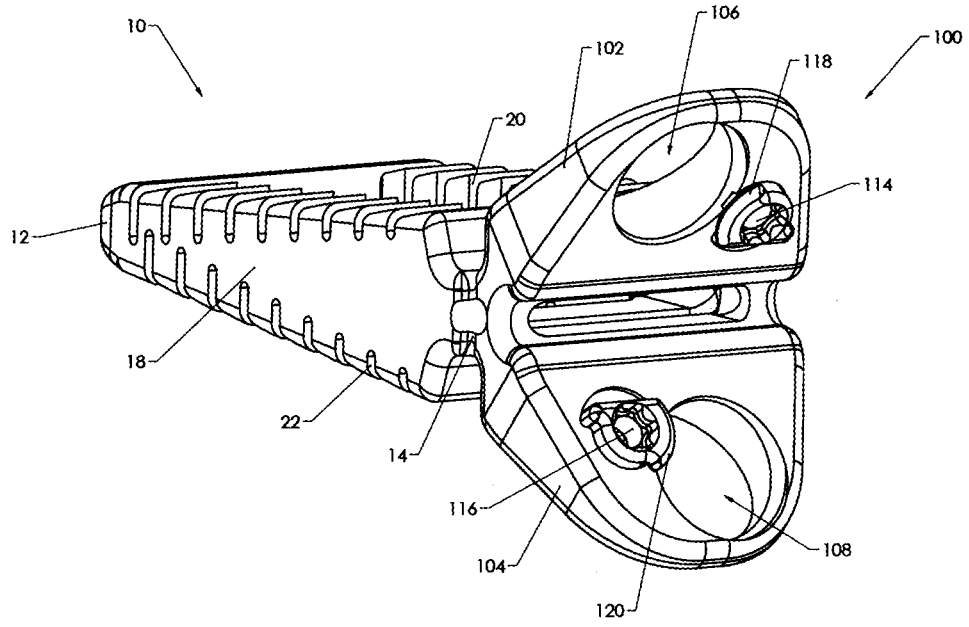
FIG. 6 is an anterior perspective view of an alternative embodiment of the wedge shaped device.
Figure 7:
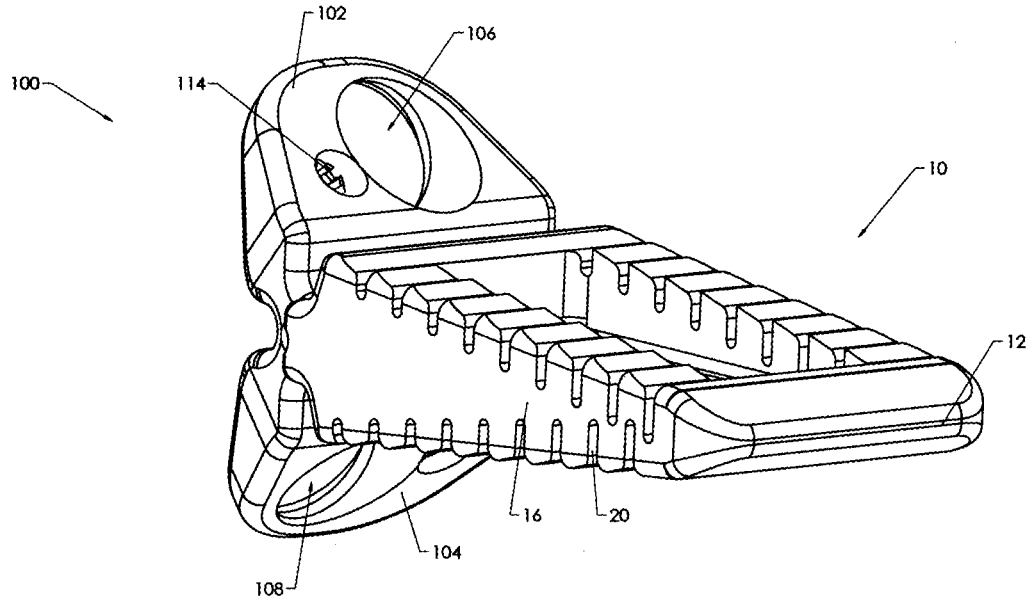
FIG. 7 is a posterior perspective view thereof.
Figure 8:
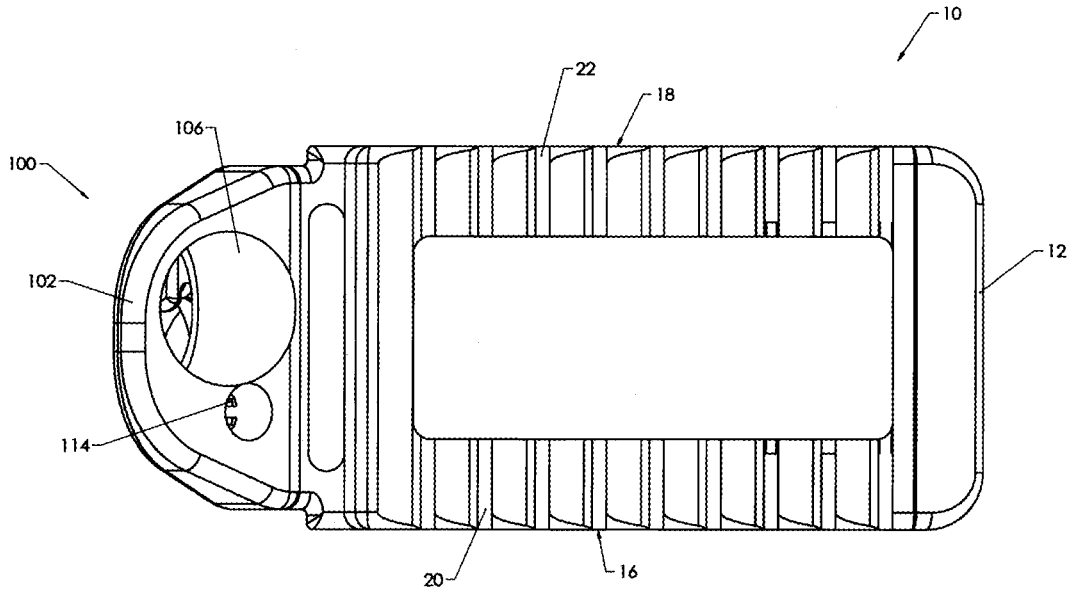
FIG. 8 is a top view thereof.
Figure 9:
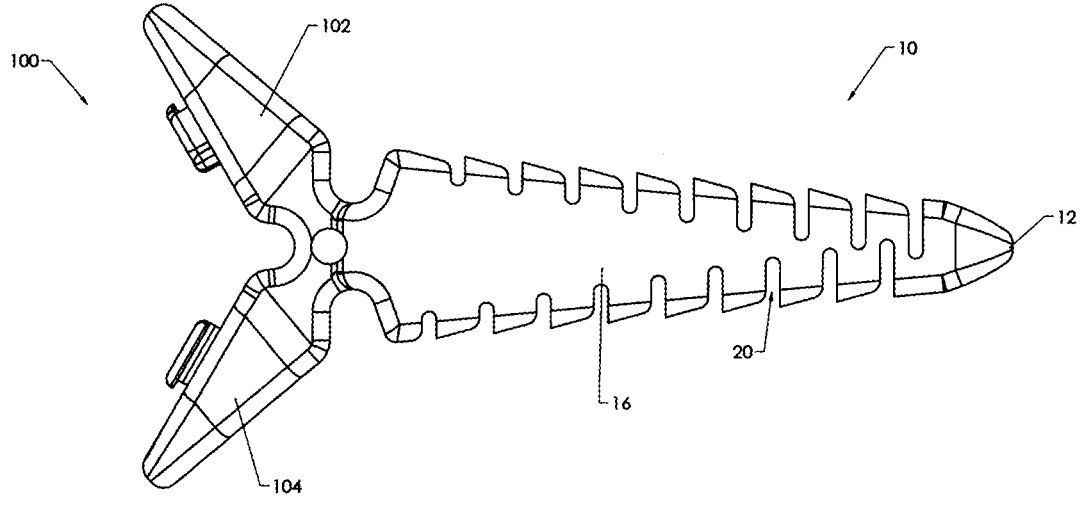
FIG. 9 is a side view thereof.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

Referring now to the Figures, disclosed is a facet joint fixation device that consists of a flexible wedge shaped implant 10 that can provide anchoring for a pedicle screw implant. The facet fixation device is preferably constructed from a single piece of biocompatible materials, such as titanium, or any conventional material used for surgical implants, such as stainless steel and its many different alloys, titanium alloys, metallic alloys, polymeric materials, plastics, plastic composites, ceramic and any other metal or material with the requisite strength and biologically inert properties. However, it is to be understood, that the various parts of the device may be constructed from various materials in some embodiments. For example, the side members may be made from a material that provides the requisite strength but also flexibility, whereas the insert end and outer end are made from a rigid material that can be subjected to force without bending or buckling. If desired, the insert end and/or the side members can be coated with a lubricant or material that provides a lubricating effect. In some embodiments, the insert end and/or the outer end may comprise one or more layers of materials, such as, for example, plastic, polymers, metals or any other biocompatible conventional material(s). In other embodiments, the device may be coated with a biocompatible material, for example, medical grade thermoplastic elastomeric compounds.

The flexible wedge shaped implant 10 is defined by an insert end 12 spaced apart from an outer end 14 by a first 16 and second 18 side members. Each side member is cut by a series of recesses 20 and 22 defining a living hinge between the insert end 12 and the outer end 14. In a preferred embodiment, the insert end 12 has a tapered tip. The recesses 20, 22 can be any shape and size as long as they provide flexibility to the side members with diminishing depths starting adjacent to the insert end 12 and extending to the outer end 14. In addition, the recesses serve the purpose of stabilizing or provide grip to prevent slippage or movement of the device. Each side member 16 and 18 is capable of being bent back and forth due to the retained thickness which provide spring hinge type resilience. The series of recesses are constructed and arranged to adjust flexibility of said implant 10. In preferred embodiments, the side members 16, 18 can flex at least about 20° relative to a horizontal axis, preferably about 45° relative to a horizontal axis, preferably about 50° relative to a horizontal axis, preferably about 75° relative to a horizontal axis, preferably 90° relative to a horizontal axis, preferably about 180° relative to a horizontal axis all of which diminishes from a first depth 30 to a minor depth 32. In some embodiments, the flexibility is about 270° relative to a horizontal axis. The first and second series of recesses 20, 22 are constructed and arranged to adjust the flexibility of the implant 10 by selectively varying the depth, width, and or spacing of the recesses 20, 22 to achieve a desired degree of flexibility.

In an alternative embodiment, the implant 10 includes a tapered end 50 which includes an outer face 52 having a first countersunk aperture 54 and a second countersunk aperture 56 for receipt of a first pedicle screw 70 and a second pedicle screw 72, respectively, to stabilize the spine, prevent movement at the surgical site, and facilitate proper spinal alignment during the fusion process. The tapered end 50 extends upwards from the outer end 14 wherein the outer face 52 is integrated with the outer end 14. In a preferred embodiment, the outer face 52 is flush with the outer end 14 and the outer end 14 in combination with the outer face 52 may be a curved surface or a planar surface having flat or curved sides or combinations thereof.

Additionally, the implant 10 ensures that the pedicle screws 70, 72 are unable to back out during the operation and healing process with the use of a locking member 74. To ensure that either pedicle screw 70, 72 does not reverse direction and remains in place after inserted between two vertebral bodies, the locking member 74 is rotatably secured to the tapered end 50 and is positioned between the first 54 and second 56 countersunk aperture. The locking member 74 includes tabs 76, 78 constructed and arranged to rotate from an installation position allowing insertion of said bone screws to a locking position to prohibit pedicle screw movement. In a preferred embodiment, the locking member 74 includes a base 80 that has a raised section elevating the locking member 74 into the installation position. Rotation of the locking member 74 from the installation position to the locking position bias the locking member 74 in the locking position wherein each the tabs 76, 78 are over the tops of the pedicle screws 70, 72.

Now referring to FIGS. 6-13, in another alternative embodiment, the implant 10 includes flexible screw wings 100 extending from the outer end 14. The alternative embodiment of the implant 10 discloses separate screw locking features and flexible screw wings 100 that accommodate various anatomical conditions. The flexible screw wings 100 includes an upper wing 102 and a lower wing 104 each extending in an approximately diagonal direction from the anterior of the implant 10. The upper wing 102 and the lower wing 104 have bone screw apertures 106, 108 to allow secure screw insertion.

Figure 10:
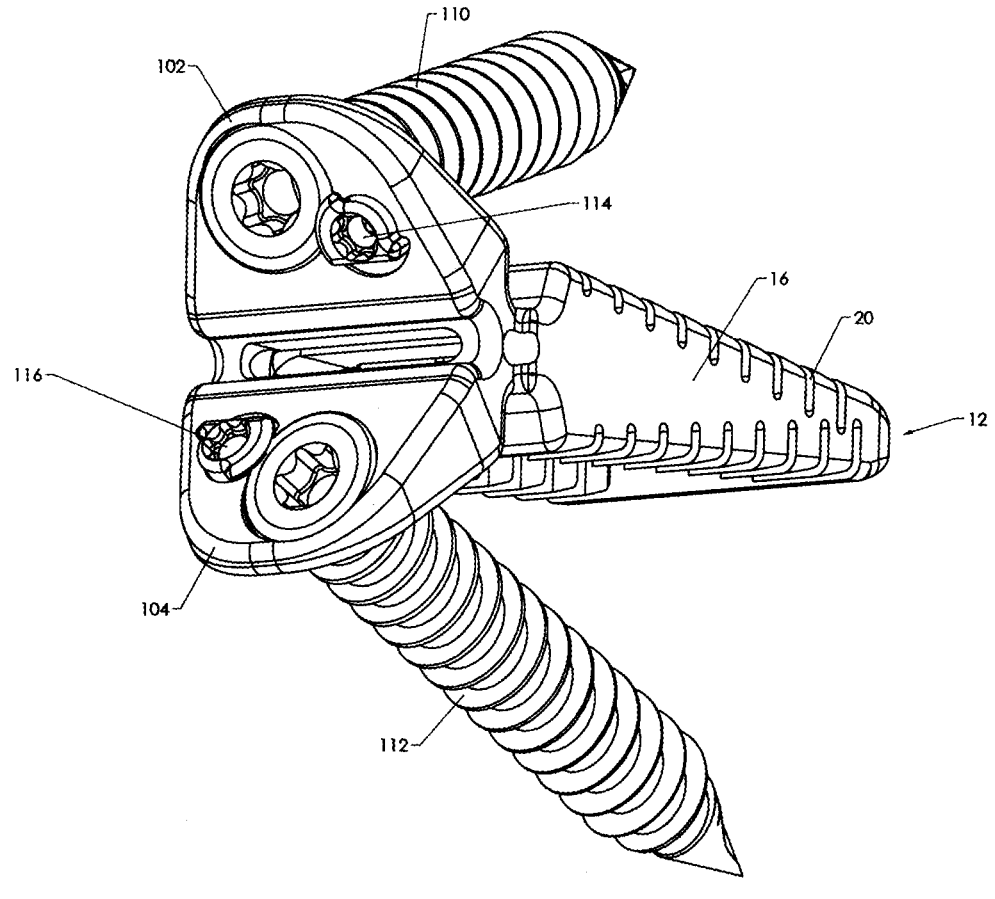
FIG. 10 is an anterior perspective view of the alternative embodiment with bone screws secured by locking mechanisms.
Figure 11:
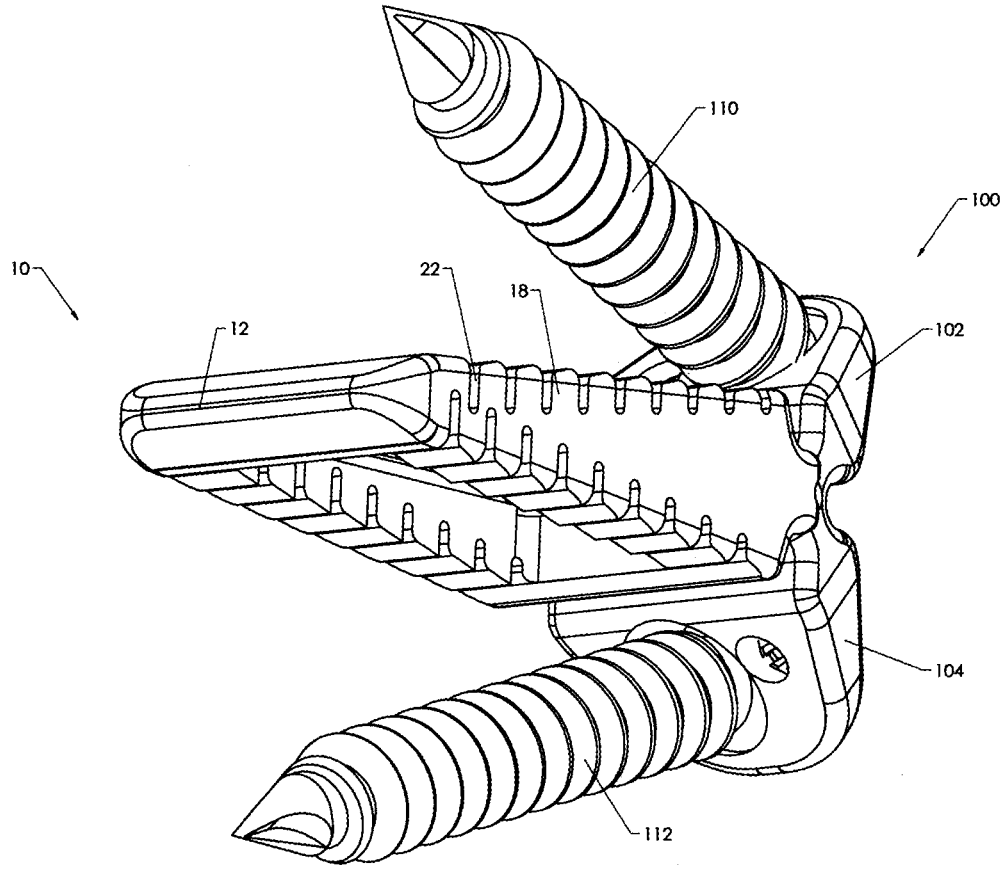
FIG. 11 is a posterior perspective view thereof.
Figure 12:
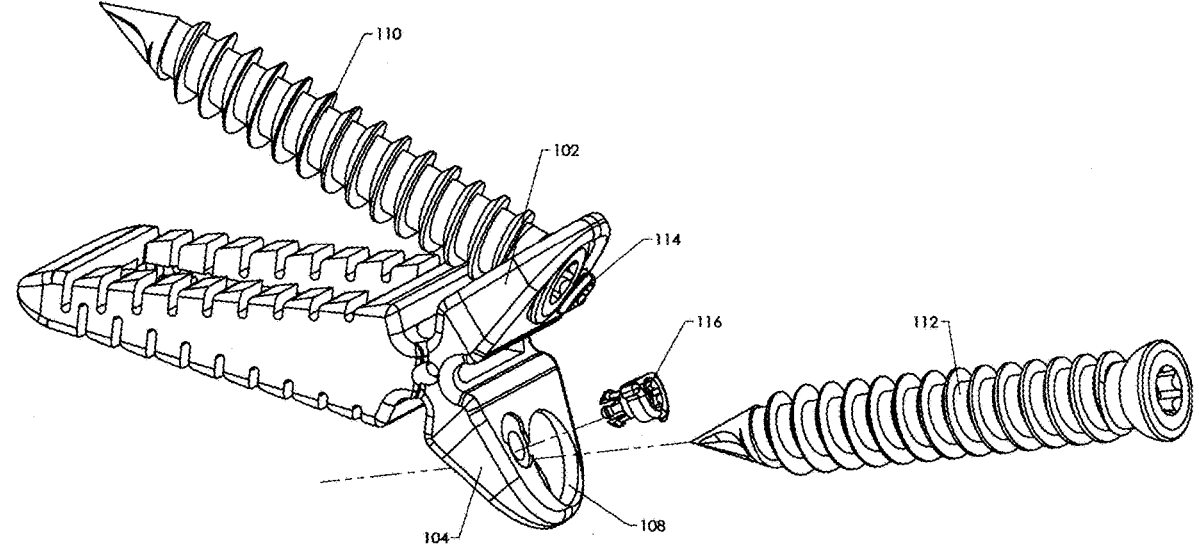
FIG. 12 is an exploded view thereof.
Figures 13A, 13B:
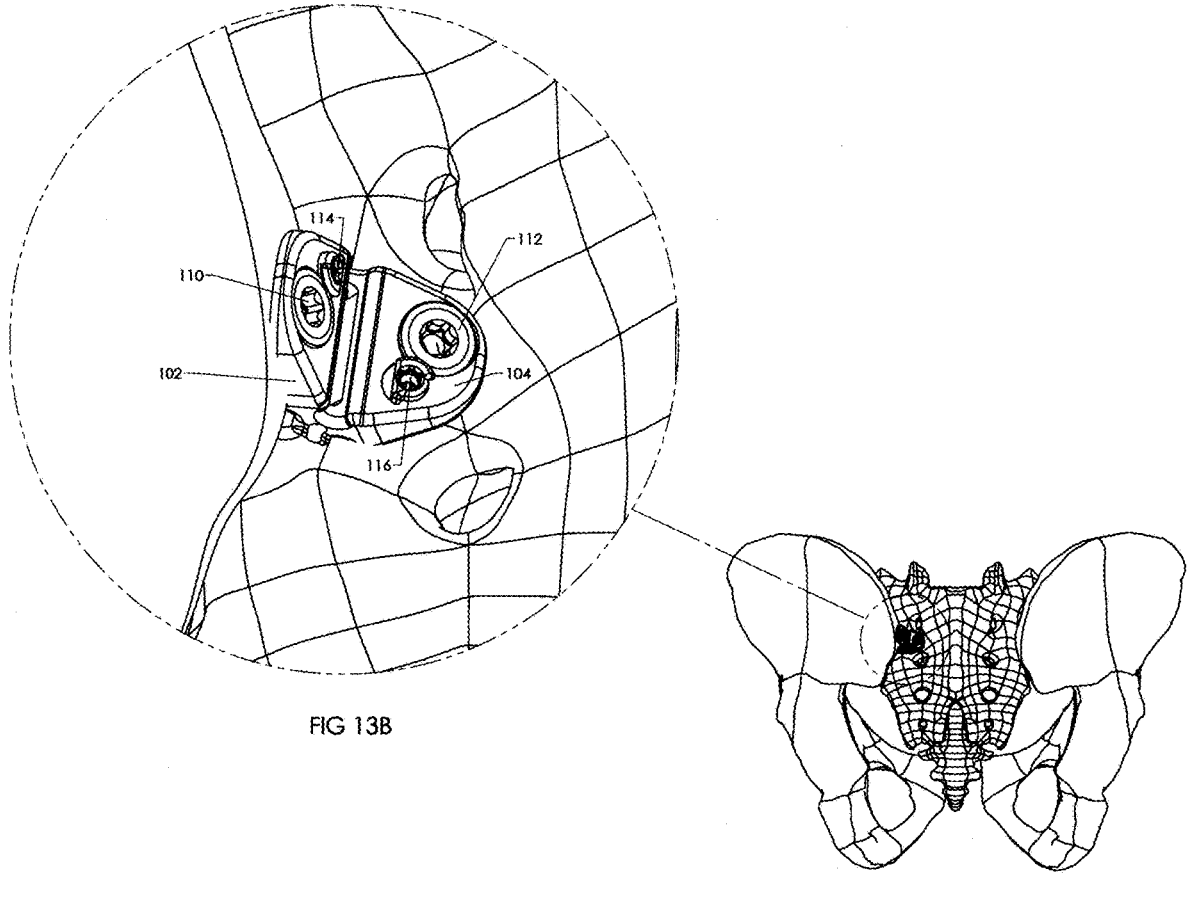
FIG. 13A is an environmental view of the wedge shaped device implanted.
FIG. 13B is a detailed view thereof.

As shown in FIGS. 10-12, each bone screw 110, 112 is inserted through the aperture 106, 108 in either the upper 102 or lower wing 104, further secured in place by locking mechanisms 114, 116 having tabs 118, 120 designed to rotate between an installation and a locking position. In the installation position, the locking mechanisms 114, 116 permit screw insertion, while in the locking position, it prevents movement of the pedicle screws 110, 112. Rotation of the locking members 114, 116 from the installation to the locking position biases the tabs 118, 120 over the tops of the pedicle screws 110, 112, securing them firmly in place.

Embodiments are also directed to methods and procedures for using the device. In a preferred embodiment, a method of implanting a pedicle screw in a patient in need thereof, comprises inserting a flexible wedge-shaped implant between adjacent vertebrae, the flexible wedge-shaped implant comprising an insert end, an outer end, wherein the insert end and the outer end are spaced apart by a first and a second side member, each side member having one or more recesses defining a hinge structure and providing flexibility. The insert end comprises a tapered end for ease of inserting the device in between adjacent vertebrae.

In preferred embodiments, the outer end comprises a planar surface having flat or curved sides or combinations thereof, and at least one opening for receiving the pedicle screw. It is to be understood that the openings may vary in size for receiving various surgical or other instruments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

What is claimed is:

1. A wedge-shaped implant comprising an insert end spaced apart from an outer end including an opening by a first side member and a second side member forming a living hinge structure defined by a retained material thickness, said first and second side members each formed from a continuous piece of material having a first side surface with a first series of recesses extending therefrom and perpendicular thereto, said first series of recesses along the insert end having a first depth, with diminishing depths extending toward said outer end; and a second series of recesses extending from a second side surface positioned adjacent to and opposing said first series of recesses, with said second series of recesses having a first depth at the insert end diminishing in depth extending towards said outer end;

wherein a thickness of each said side member, measured between said first and second side surfaces, remains uniform along a length of said living hinge structure;

wherein said first and second series of recesses cooperate across said retained material thickness to define said living hinge structure configured to elastically flex along said length of said living hinge structure;

whereby said insert end can be offset from said outer end by flexure of said living hinge structure, and wherein an effective hinge profile defined by said recesses gradually reduces along said length of said living hinge structure from said outer end to said insert end.

2. The wedge-shaped implant of claim 1, wherein said insert end includes a tapered tip.

3. The wedge-shaped implant of claim 1, wherein said opening formed in the outer end comprises a threaded receptacle configured for releasable engagement during insertion of the wedge-shaped implant.

4. The wedge-shaped implant of claim 1 wherein the insert end and the outer end are rigid.

5. The wedge-shaped implant of claim 1 wherein said first series of recesses and said second series of recesses are constructed and arranged to adjust flexibility of said implant.

6

6. The wedge-shaped implant of claim 1 wherein said wedge-shaped implant includes a tapered end extending upwards from said outer end having an outer face including a first countersunk aperture for receipt of a first pedicle screw and a second countersunk aperture for receipt a second pedicle screw.

7. The wedge-shaped implant of claim 6 wherein said outer face is integrated with said outer end.

8. The wedge-shaped implant of claim 6 wherein said outer face is flush with said outer end, said outer end in combination with said outer face is a curved surface or a planar surface having flat or curved sides or combinations thereof.

9. The wedge-shaped implant of claim 6 wherein a locking member is rotatably secured to said tapered end, said locking member positioned between the first and second countersunk apertures.

10. The wedge-shaped implant of claim 9 wherein said locking member includes a base having a raised section elevating said locking member into an installation position wherein rotation of said locking member from said installation position to a locking position biases said locking member in said locking position wherein a plurality of tabs extending from said locking member are constructed and arranged to rotate from an installation position allowing insertion of bone screws to a locking position to prohibit pedicle screw movement.

\* \* \* \* \*